United States Patent [19]
Heffelfinger et al.

[11] Patent Number: 5,799,773
[45] Date of Patent: Sep. 1, 1998

[54] METHOD AND APPARATUS FOR CORRECTING LENS AND DETECTOR NON-UNIFORMITIES

[75] Inventors: David M. Heffelfinger, San Pablo; Craig Van Horn, Sebastapol, both of Calif.

[73] Assignee: Bio-Rad Laboratories, Inc., Hercules, Calif.

[21] Appl. No.: 814,125

[22] Filed: Mar. 10, 1997

[51] Int. Cl.⁶ .................................................. G01N 27/26
[52] U.S. Cl. .......................... 204/461; 204/452; 204/603; 204/612
[58] Field of Search ................... 204/451, 452, 204/456, 461, 466, 606, 612, 601, 603, 616

[56] References Cited

U.S. PATENT DOCUMENTS

| | | | |
|---|---|---|---|
| 5,294,323 | 3/1994 | Togusari et al. | 204/612 |
| 5,307,148 | 4/1994 | Kambara et al. | 356/344 |

*Primary Examiner*—Kathryn L. Gorgos
*Assistant Examiner*—Alex Noguerola
*Attorney, Agent, or Firm*—David G. Beck; Townsend and Townsend and Crew

[57] ABSTRACT

A method and apparatus for correcting an image of an electrophoresis gel for lens and detector non-uniformities is provided. The removal of such non-uniformities, in conjunction with a uniform illumination source, allows quantitative measurements of an electrophoresis gel to be made, thus increasing the information which can be obtained from an electrophoretic analysis. Lens and detector non-uniformities are removed by first determining the magnitude of the non-uniformities using a calibration standard. The calibration standard has a uniform emittance, preferably in the same wavelength band as the labeled regions of the electrophoresis gel. By placing the calibration standard in close proximity to the entrance aperture of the lens, the calibration process is relatively insensitive to illumination source non-uniformities. Thus an image of the calibration standard taken with the same lens settings as the unknown provides detailed information on the lens and detector non-uniformities. This information in conjunction with a darkfield image is used to correct the sample image.

15 Claims, 5 Drawing Sheets

METHOD AND APPARATUS FOR CORRECTING LENS AND DETECTOR NON-UNIFORMITIES

The present invention relates generally to electrophoresis reading systems and, more particularly, to a method and apparatus for removing lens and detector non-uniformities from an electrophoresis system.

BACKGROUND OF THE INVENTION

In the biotechnical field, fluorescent dyes are routinely used as sensitive, non-isotopic labels. These labels are used to identify and locate a variety of cell structures, ranging from malignant tumors to specific chromosomes in a DNA sequence. A variety of devices have been designed to read fluorescent-labeled samples.

Gel electrophoresis is one technique commonly used in conjunction with fluorescent dyes and other markers to identify specific molecules as well as other tagged units. In this technique an electric field is used to cause the migration of the tagged units through a gel or other solution.

In U.S. Pat. No. 4,874,492 a gel electrophoresis system is disclosed in which samples are treated with fluorescent markers prior to applying them to an electrophoretic gel. The gel is illuminated with a UV source and the fluorescence pattern is detected with a cooled charge-coupled-device (CCD) two-dimensional detector array. The CCD array is cooled to at least −25 degrees C. in order to improve light sensitivity and increase the dynamic range.

In U.S. Pat. No. 5,162,654 a system is disclosed to optically determine which of four fluorophores is fluorescing in an eletrophoresis gel. Fluorescence emitted by the gel passes first through four separate band pass filters and then through four wedge prisms. As a result of this optical configuration, the emitted fluorescence is imaged on four discrete areas on the detector array. The specific fluorophore excited by the irradiation source is determined by comparing the relative intensities of the fluorescence detected in the four detection areas.

In U.S. Pat. No. 5,294,323 the disclosed gel electrophoresis system utilizes a vertical electrophoresis plate. A laser beam passes horizontally through the gel in a direction perpendicular to the longitudinal axis of the electrophoresis plate. The emitted fluorescence is reflected to a solid state imaging sensor such that the reflected pattern is parallel to the direction of the laser beam.

In U.S. Pat. No. 5,324,401 a fluorescence detection system for capillary electrophoresis is disclosed which provides for the simultaneous excitation and detection of fluorescent probes within a plurality of capillaries. The excitation source is a laser which is coupled to the capillaries through an optical fiber bundle. The fluorescence from the capillary array is focussed through a lens and imaged onto a CCD camera for analysis.

In a paper by Sutherland et al. entitled "Electronic Imaging System for Direct and Rapid Quantitation of Fluorescence from Electrophoretic Gels: Application to Ethidium Bromide-Stained DNA" published in *Analytical Biochemistry* 163, 446–457 (1987), the authors describe an imaging system which uses a CCD camera. The CCD camera quantifies the fluorescence received from electrophoretic gels, chromatograms, and other sources. The paper describes several sources of non-uniformities which impact the ability of the system to obtain accurate results.

From the foregoing, it is apparent that an improved electrophoresis apparatus is desired which enables accurate quantitative measurements of fluorescence to be made.

SUMMARY OF THE INVENTION

The present invention provides a method and apparatus for calibrating the lens and detector assemblies of an imaging apparatus such as an electrophoresis gel system. Once the lens and detector assemblies have been calibrated, non-uniformities exhibited by either may be removed from the sample image. If the light source illuminating the sample is uniform, quantitative measurements of an electrophoresis gel can be made, thus increasing the information which can be obtained from the electrophoretic analysis.

The non-uniformities in the lens and detector assemblies are determined through the use of a reference or calibration standard which exhibits uniform fluorescence. An image of the standard is taken using the same lens settings as used with the unknown, thus insuring that the calibration image correctly reflects the system non-uniformities as applied to the unknown. The image of the calibration standard along with a darkfield image are used to correct the sample image.

In one embodiment of the invention a calibration standard is contained within a filter wheel, the filter wheel proximate the entrance to the lens assembly. After a sample image is taken, the filter wheel rotates in order to place the calibration standard immediately in front of the lens. An image of the calibration standard is taken followed by a darkfield image. The darkfield image is taken by closing a shutter to the detector, thus preventing source light, fluorescence, or any other source of illumination from reaching the detector. The image is corrected by applying a simple algorithm which uses both the calibration standard image and the darkfield image.

A further understanding of the nature and advantages of the present invention may be realized by reference to the remaining portions of the specification and the drawings.

DESCRIPTION OF THE PREFERRED EMBODIMENT

Figure 1:
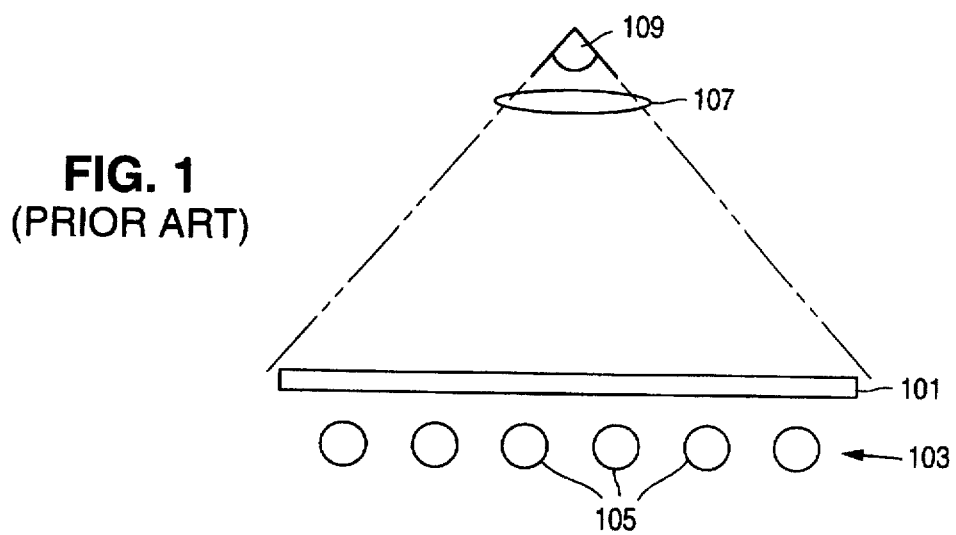
FIG. 1 is an illustration of a cross-section of a gel electrophoresis apparatus according to the prior art.

FIG. 1 is an illustration of a cross-section of a gel electrophoresis apparatus according to the prior art. In this system a gel plate 101 is illuminated by a light source 103. Light source 103 is comprised of a plurality of individual light bulbs 105. The light from source 103 causes fluorophores or other fluorescing material contained within specific areas of sample 101 to fluoresce. The emitted fluorescence passes through one or more lenses 107 and is imaged onto a detector 109. Based upon the received fluorescence from sample 101, it is possible to determine the areas of fluorescence on sample 101.

Although the intensity of the fluorescence from sample 101 contains additional information such as the quantity of the fluorescing material, to date the ability to quantify this information has been limited due to non-uniformities in the illumination source, the imaging optics, and the detector.

One method of eliminating the effects of non-uniformities in the lens and in the detector is through the use of a reference or calibration standard. During calibration, the standard replaces the sample. A suitable calibration standard is a piece of fluorescent glass or plastic which uniformly fluoresces when illuminated with a source. Preferably the standard fluoresces at the same wavelength as the labels used with the sample, thus insuring that the standard accurately reproduces the non-uniformities of the lens and the detector.

In practice, the user first takes an image represented by $I_1(x,y)$ of the sample in question. The sample is then replaced with the standard and a second image, $I_2(x,y)$, is taken. The second image is known as a flatfield image. To obtain a corrected image a third exposure must be made in which the camera shutter is blocked completely. The third image, $D_0(x,y)$, represents the darkfield. The corrected image, $CI(x,y)$, is represented by:

$$CI(x,y)=[\{I_1(x,y)-D_0(x,y)\}/\{I_2(x,y)-D_0(x,y)\}]*M$$

where M is equal to the average $I_2(x,y)$

Although the above technique can be used to obtain accurate and therefore quantifiable images of the sample, assuming a uniform illumination source, the technique is impractical for many applications. The technique requires the user to change samples and make a series of measurements in order to obtain a single corrected image.

Figure 2:
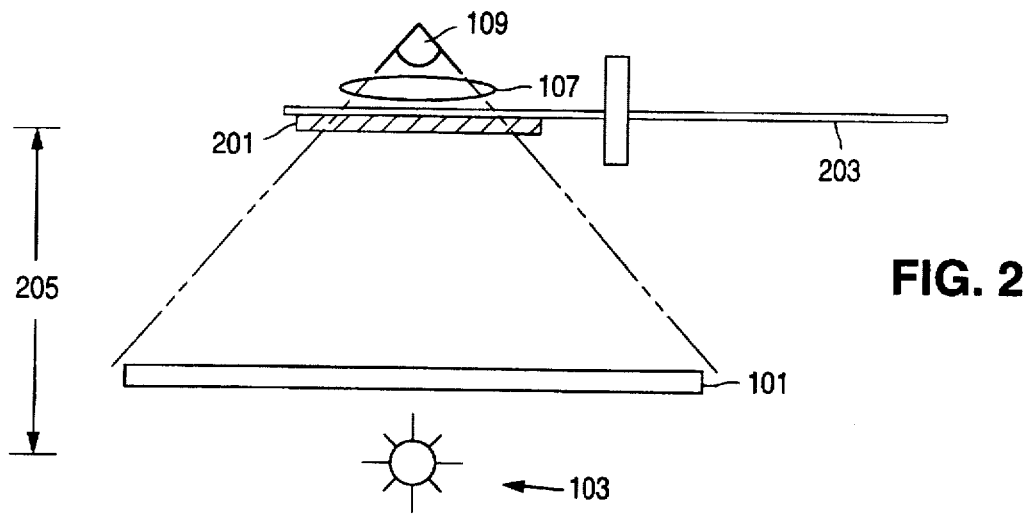
FIG. 2 is an illustration of an embodiment of the invention.

FIG. 2 is an illustration of one embodiment of the invention. As in the prior system, fluorescence from a sample 101 is imaged onto a detector 109 by a lens 107. In this embodiment, if the user wishes to obtain a corrected image, a calibration standard 201 is moved into place with a stage 203. In the preferred embodiment of the invention, standard 201 is placed in close proximity to the entrance aperture of lens 107. Preferably stage 203 is a rotation stage. As in the previous technique three images are required; a sample image, a calibration image, and a darkfield image. The equation to obtain the corrected image is the same as that given above.

Figure 3:
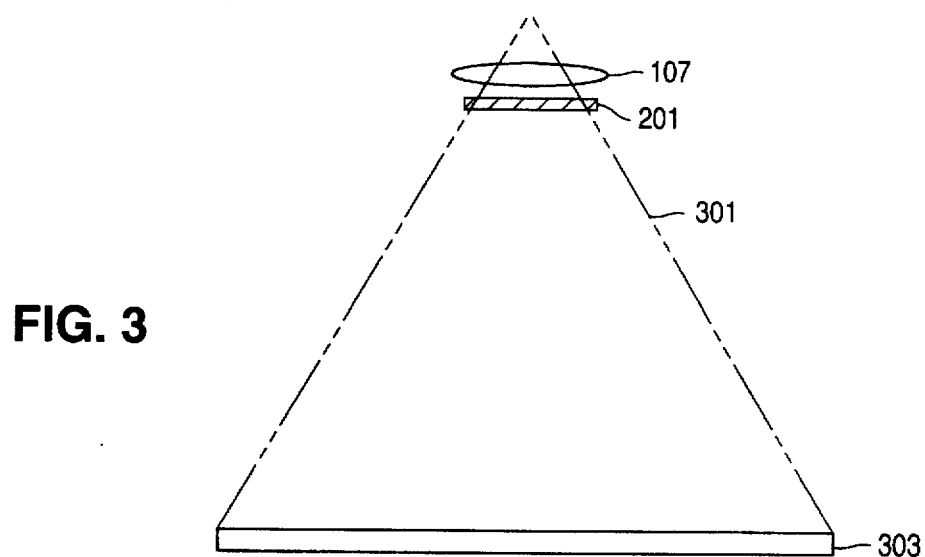
FIG. 3 illustrates the relationship between the lens aperture and the size of the calibration standard.

In order to obtain an accurate mapping of the non-uniformities of the lens, calibration standard 201 must completely fill the aperture of the lens. However, since standard 201 is much closer to lens 107 than a standard placed at the sample plane as in the previous system, standard 201 may be much smaller. This relationship is illustrated in FIG. 3. The collection aperture is represented by dotted lines 301. As illustrated, standard 201 is approximately the same size as lens 107 due to its close proximity to the lens. However, a standard 303 placed at the sample plane must be much larger in order to fill the lens aperture, thus increasing fabrication costs and difficulty.

Although the present invention may be used to overcome the non-uniformities associated with the lens and the detector, in order to quantify a sample image the illumination source must be uniform. If the source is not uniform, the inaccuracies associated with the sample image, $I_1(x,y)$, will not be completely removed by the technique of the invention. Illumination uniformity may be achieved using multiple light sources, reflectors, masks, or scanning light systems.

Light uniformity is not, however, required during the calibration step of the preferred embodiment of the present invention. Although increased light uniformity may increase the accuracy of the described calibration technique, given the distance 205 separating light source 103 from standard 201, illumination uniformity is not a requirement for this technique.

Figure 4:
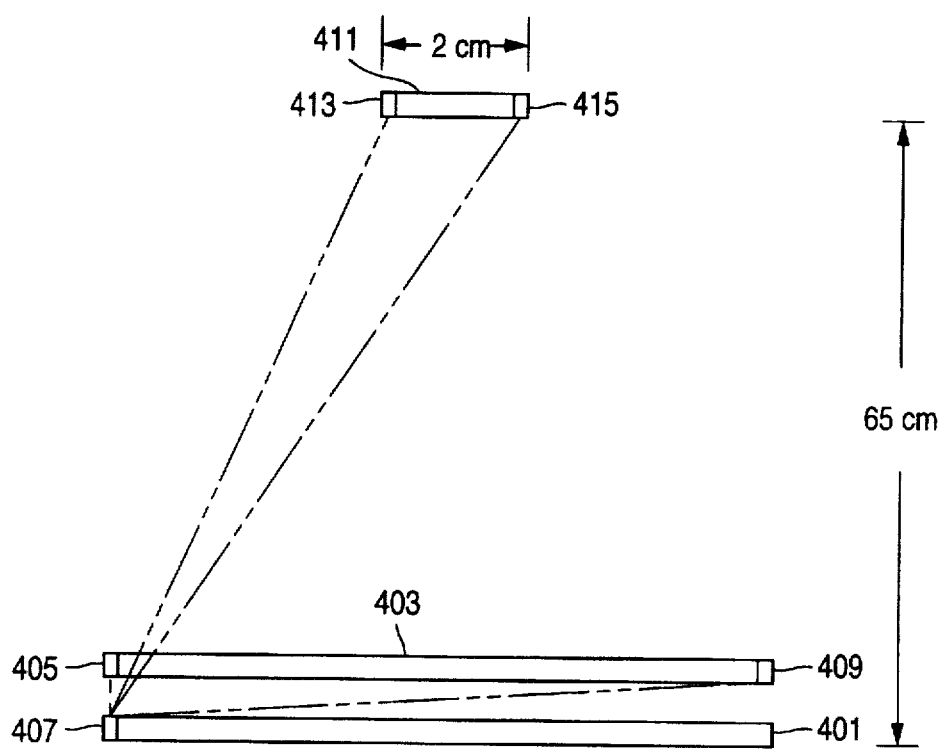
FIG. 4 illustrates the relationship between light uniformity and the calibration standard.

FIG. 4 illustrates the relationship between light uniformity and the placement of the calibration standard. A light source 401 illuminates a calibration standard 403 placed in close proximity to light source 401. As defined by Lambert's Law, the intensity of a small incremental area of the source, $J_\theta$, is equivalent to the intensity of the incremental area in the direction of the normal, $J_0$, times the cosine of the angle $\theta$ as measured from the surface normal. Therefore the intensity measured at a point 405 on standard 403 which is directly above an area 407 of source 401 is equivalent to the intensity of area 407. In contrast, the intensity measured at a point 409 at the opposite end of standard 403 is significantly reduced. For example given an angle $\theta$ of 80 degrees, the intensity at point 409 is only 17 percent of the intensity measured at point 405. Thus if source 401 is non-uniform, calibration standard 403 will be non-uniformly illuminated, resulting in a calibration technique which is a function not only of lens and detector non-uniformities, but also a function of illumination non-uniformities.

In contrast, if a calibration standard is used which is located at some distance from source 401, the illumination non-uniformities have little impact on the calibration technique. For example, assuming that a calibration standard 411 measuring 2 centimeters in diameter is located 65 centimeters from source 401, there is less than 1 percent difference in intensity as measured at points 413 and 415. Thus by placing the calibration standard near the lens and at a distance from the source, the effects of illumination non-uniformities can be greatly minimized.

Figure 5:
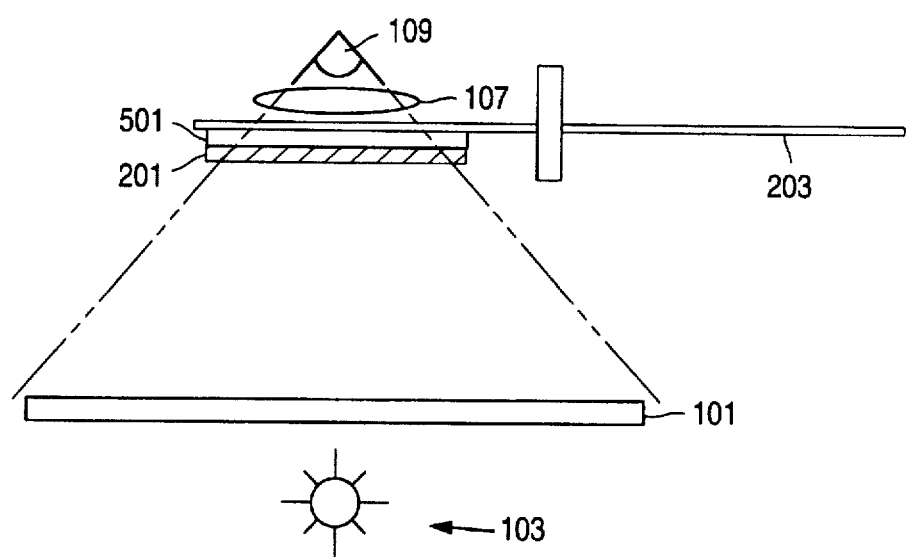
FIG. 5 is an illustration of an alternate embodiment of the invention utilizing a diffuser in conjunction with the calibration standard.

FIG. 5 is an illustration of an alternate embodiment of the invention. This embodiment contains the same elements as illustrated in FIG. 2 with the addition of a diffuser 501. Diffuser 501 is mounted between calibration standard 201 and lens 107. Diffuser 501 insures that the system only monitors the non-uniformities of the lens and detector by smoothing out even the small non-uniformities within the calibration standard.

Figure 6:
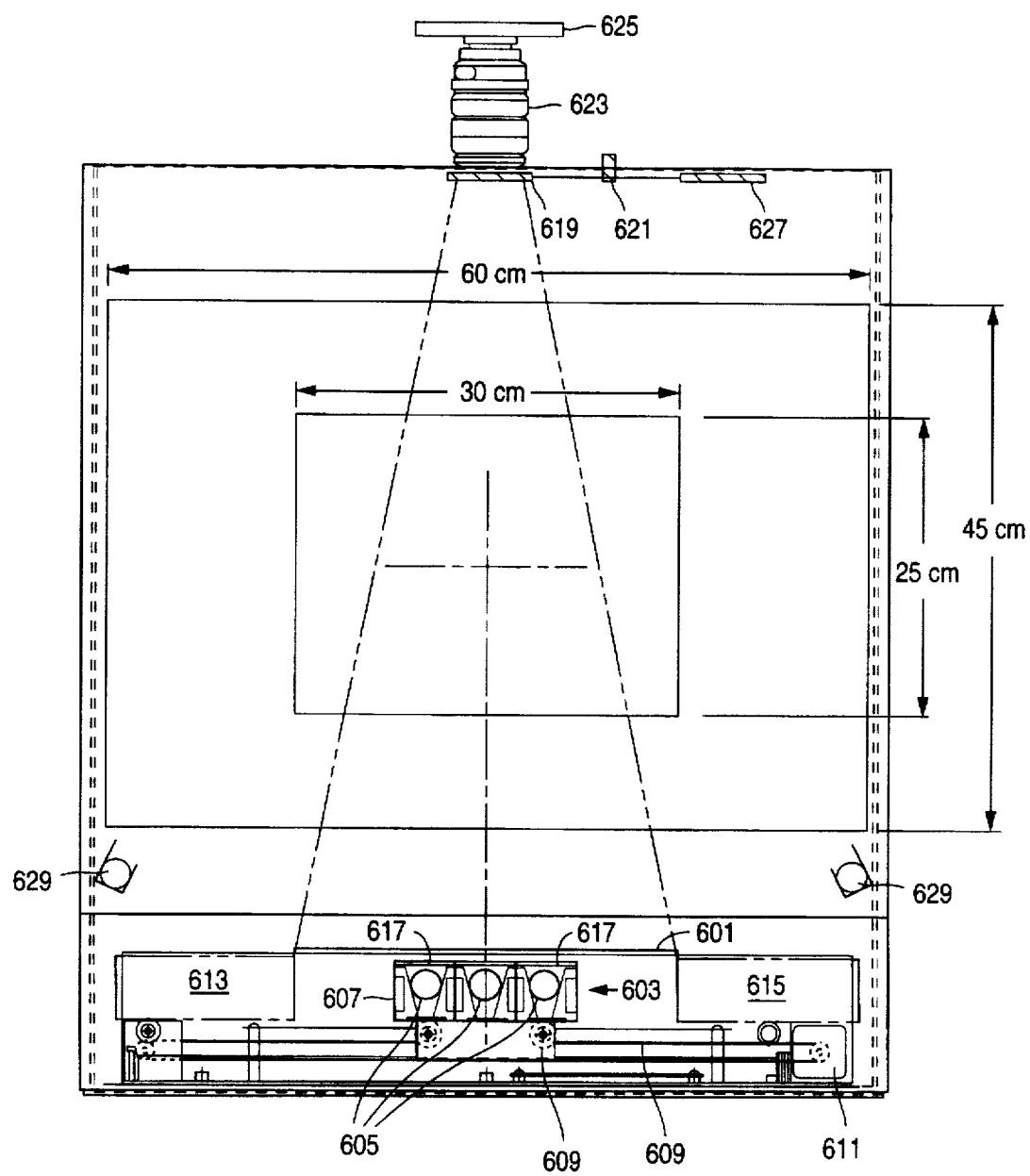
FIG. 6 is a detailed illustration of an embodiment of the invention.

FIG. 6 is a detailed illustration of an embodiment of the invention. In this embodiment a sample 601 is illuminated with a light source 603. Source 603 is comprised of three individual light bulbs 605 which are disposed within a tray 607. Tray 607 rides on a pulley and belt system 609 which is controlled by a motor 611. During the sampling period, light tray 607 scans sample 601, starting at a point 613 and ending at a point 615. The scan rate, the intensity of the source, and any intervening filters 617 determine the intensity of the radiation illuminating sample 601, resulting in the fluorescence of appropriately marked regions of sample 601. Scanning source 603 insures that the illumination is uniform.

Emitted fluorescence from sample 601 passes through either an aperture 619 or a filter 619 in a filter wheel 621 prior to being imaged by a lens assembly 623 onto a detector 625. In this embodiment detector 625 is a CCD detector, preferably a two dimensional array. When a calibration image is required, filter wheel 621 rotates in order to place a calibration standard 627 in front of the lens assembly.

There are several ways in which calibration standard 627 may be illuminated. First, radiation passing through sample 601 from source 603 may be used. Due to the pattern on gel sample 601, the illumination intensity will be quite non-uniform. However, as shown above, this standard is relatively insensitive to illumination non-uniformities. Source 603 may either be used in the normal scanning mode or maintained in a stationary position at the center of the apparatus. Second, sample 601 may be removed and source 603 used in either a scanning or stationary mode. Third, a separate source 629 may be used to illuminate calibration standard 627. Preferably source 629 is positioned above the sample plane as shown, thus not requiring the removal of sample 601 prior to taking a calibration image. In the preferred embodiment a pair of sources 629 are used to illuminate standard 627, thus improving the uniformity of the light reaching standard 627.

Figure 7:
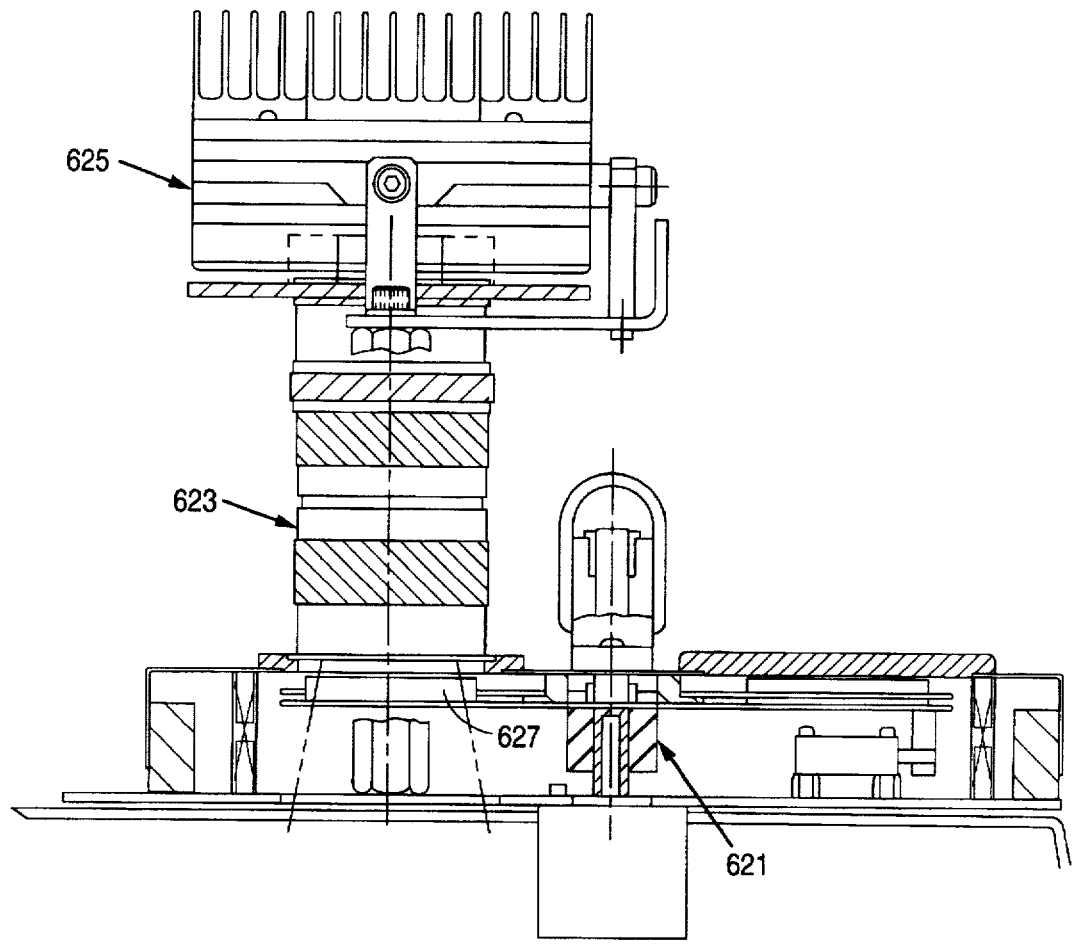
FIG. 7 is a close-up view of the detector assembly, lens assembly, and filter wheel of the embodiment illustrated in FIG. 6.

FIG. 7 is a close-up view of detector assembly 625, lens assembly 623, and filter wheel 621. As illustrated, calibration standard 627 has been rotated into place in readiness for a calibration measurement.

Figure 8:
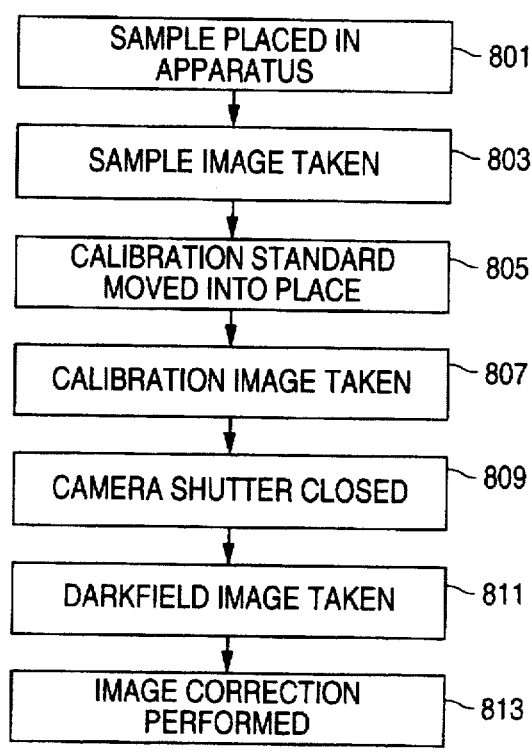
FIG. 8 is a block diagram illustrating the process steps of the invention.

FIG. 8 is a block diagram illustrating the process steps of the present invention. Initially a sample is placed in the testing apparatus (step 801). Although the invention is not limited to gel electrophoresis applications, this is one of the most common applications. In this instance the sample is a gel in which certain regions, structures, or molecules have been labeled with a fluorescent marker which fluoresces at a specific wavelength when irradiated at the marker's excitation wavelength. The emission wavelength is different from the excitation wavelength, thus allowing the emission to be distinguished from the source through the use of filters. The emission from the selected regions is imaged onto a detector in order to form an image of the sample (step 803). Once a sample image has been taken, a calibration standard is moved into place (step 805). In order to properly measure the non-uniformities of the lens and detector assemblies, the system aperture and magnification settings are not changed from those used during the sample imaging step. A calibration image is taken (step 807) using either the sample illumination source or an alternate source as described above. The camera shutter is then closed (step 809) and a darkfield image is taken (step 811). The sample image is then corrected (step 813) using well known mathematical relationships such as the correction algorithm given above.

Figure 9:
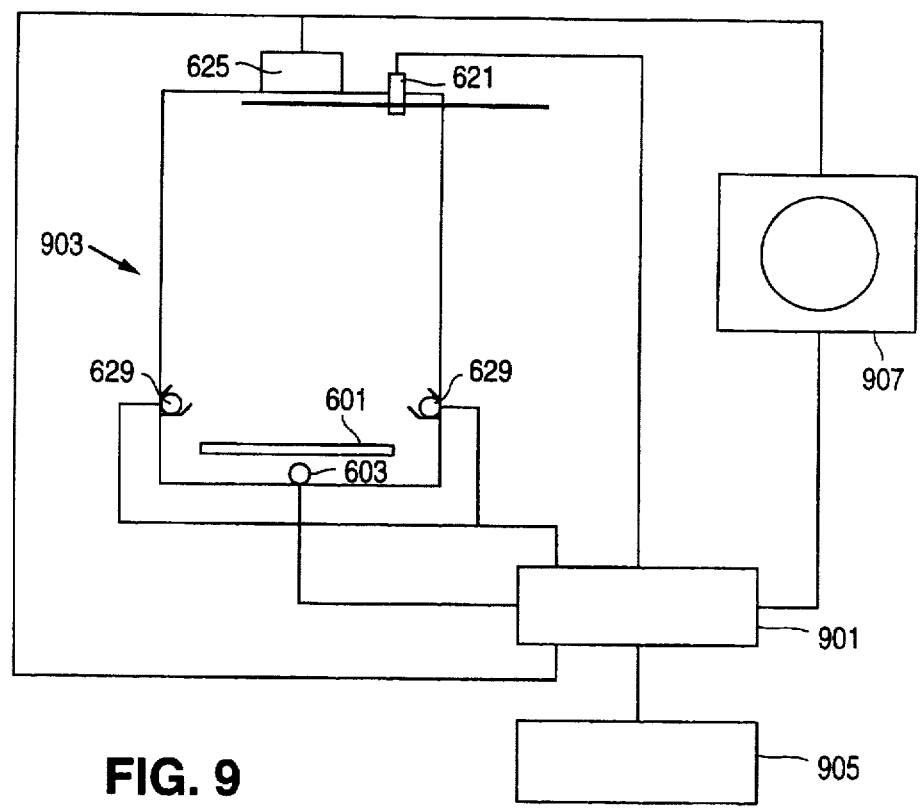
FIG. 9 is an illustration of the major components of a system according to the preferred embodiment of the invention.

FIG. 9 is an illustration of the major components of a system according to the preferred embodiment of the invention. In this embodiment the key system components are connected to a processor 901. Processor 901 permits the entire process to be automated, thus making the correction process straightforward and minimizing the risk of user errors. To use the system, sample 601 is first placed within electrophoresis apparatus 903. The user then manually sets the aperture and magnification of the system unless the system has been designed to automatically select these parameters. In the preferred embodiment, the user then enters into processor 901, through a user interface 905, the marker (e.g., fluorophores) in use on sample 601. Based on this information processor 901 uses an integrated look-up table to determine the appropriate excitation and emission settings. Processor 901 then moves an appropriate filter in place by manipulating filter wheel 621.

Once the system operating parameters have been set, either manually or automatically, the user initiates a run by sending an appropriate signal to processor 901 through interface 905. Processor 901 then turns on source 603 and takes an image of sample 601. If source 603 is a scanning source as shown in FIG. 6, processor 901 also control the scanning operation by controlling scanning motor 611.

The image taken by detector 625 is stored in memory resident within processor 901 as well as being displayed on a monitor 907. If detector 625 is a CCD camera, the data is easily stored in a digital format, thus making later data manipulation easy. Depending upon the configuration of processor 901, several different operations can take place next. If the system is in a completely automatic mode, the system will automatically begin the process of correcting the sample image. In this mode an initial uncorrected image may or may not be shown, depending upon the system set-up. The benefit of showing the initial image is that the user may be able to determine that the image contains no useful data and thus end the cycle prior to the correction technique being applied.

In the automatic mode, after a sample image has been taken, processor 901 turns off source 603 and moves a calibration standard into place. Since the calibration standard is within filter wheel 621, processor 901 simply rotates the wheel until the appropriate filter recess is in place. Processor 901 then activates the appropriate illumination source, either source 603 or alternate sources 629, and takes a flatfield image. The data from this image is stored in the resident processor memory. After the calibration standard image has been completed, processor 901 closes a shutter to camera assembly 625 and takes a darkfield image. Using these two additional images, processor 901 corrects the sample image and presents the corrected image on monitor 907. Both the uncorrected and the corrected images as well as the flatfield and darkfield images can be stored for later retrieval and use.

As will be understood by those familiar with the art, the present invention may be embodied in other specific forms without departing from the spirit or essential characteristics thereof. For example, this invention is not limited to specific excitation and emission wavelengths. As such, UV excited markers which fluoresce in the visible wavelengths may be used. Accordingly, the disclosures and descriptions herein are intended to be illustrative, but not limiting, of the scope of the invention which is set forth in the following claims.

We claim:

1. A calibration system for an electrophoretic apparatus, comprising:

a platform that is holding an electrophoresis gel;

a light source that irradiates said electrophoresis gel;

a lens assembly that images an emittance from a labeled region of said electrophoresis gel onto a detector;

a calibration standard, said calibration standard exhibiting uniform emittance when excited; and a movable stage coupled to said calibration standard, wherein said movable stage has at least a first position and a second position, wherein said movable stage in said first position places said calibration standard proximate to an entrance aperture of said lens assembly, and wherein said movable stage in said second position places said calibration standard outside of said lens assembly entrance aperture.

2. The calibration system of claim 1, wherein said uniform emittance of said calibration standard is in a first wavelength band, and wherein said emittance from said labeled region is within said first wavelength band.

3. The calibration system of claim 1, wherein said calibration standard fluoresces when excited.

4. The calibration system of claim 1, further comprising a diffuser interposed between said calibration standard and said lens assembly.

5. The calibration system of claim 1, wherein said calibration standard is excited by said light source.

6. The calibration system of claim 1, wherein said calibration standard is excited by a second light source.

7. The calibration system of claim 1, further comprising a shutter coupled to said detector.

8. The calibration system of claim 1, wherein said light source emits illumination uniform to within 5 percent over an area of said electrophoresis gel.

9. A system for calibrating an electrophoretic apparatus, comprising:

- a platform that is holding an electrophoresis gel;
- a light source that irradiates said electrophoresis gel;
- a lens assembly that images said electrophoresis gel onto a detector, said image of said electrophoresis gel including at least one labeled region, said labeled region fluorescing when irradiated by said light source, wherein said detector generates a first output signal corresponding to said image of said electrophoresis gel;
- a calibration standard, said calibration standard exhibiting uniform fluorescence when excited, said uniform fluorescence imaged by said lens assembly onto said detector, wherein said detector generates a second output signal corresponding to said image of said calibration standard;
- a movable stage coupled to said calibration standard, wherein said movable stage has at least a first position and a second position, wherein said movable stage in said first position places said calibration standard proximate to an entrance aperture of said lens assembly, and wherein said movable stage in said second position places said calibration standard outside of said lens assembly entrance aperture;
- a shutter coupled to said detector, said shutter having an open position and a closed position, wherein said shutter in said closed position prevents light from entering said detector, wherein said detector generates a third output signal with said shutter in said closed position;
- a processor coupled to said detector, wherein said processor stores said first, second, and third detector output signals, and wherein said processor determines a corrected electrophoresis gel image using said first, second, and third detector output signals, wherein said processor removes lens non-uniformities and detector non-uniformities from said electrophoresis gel image to form said corrected electrophoresis gel image; and
- a display coupled to said processor for displaying said corrected electrophoresis gel image.

10. The calibration system of claim 9, wherein said processor controls said shutter and said movable stage.

11. The calibration system of claim 9, wherein said light source uniformly illuminates said electrophoresis gel.

12. The calibration system of claim 9, wherein said processor controls a second light source for illuminating said calibration standard.

13. The calibration system of claim 9, wherein said light source is a scanning source, and wherein said processor controls said scanning source.

14. A method of removing lens assembly non-uniformities and detector non-uniformities from an image of an electrophoresis gel, the method comprising the steps of:

- irradiating said electrophoresis gel with a light source, wherein at least one labeled region of said irradiated gel fluoresces;
- imaging said irradiated electrophoresis gel onto a detector using a lens assembly;
- outputting a first signal to a processor, said first signal corresponding to said image of said irradiated electrophoresis gel ;
- irradiating a calibration standard with a calibration standard illuminator, said calibration standard illuminator selected from the group consisting of said light source and a second source, wherein said calibration standard uniformly fluoresces when irradiated with said calibration standard illuminator, and wherein said calibration standard is located proximate an entrance aperture of said lens assembly;
- imaging said calibration standard onto said detector using said lens assembly to form a calibration standard image, wherein said calibration standard image contains information corresponding to said lens assembly non-uniformities and said detector non-uniformities;
- outputting a second signal to said processor, said second signal corresponding to said calibration standard image;
- closing a shutter leading to said detector to form a darkfield image on said detector;
- outputting a third signal to said processor, said third signal corresponding to said darkfield image; and
- determining a corrected image of said electrophoresis gel with said processor, wherein said corrected image has said lens assembly non-uniformities and said detector non-uniformities removed.

15. The method of claim 14, wherein said irradiating said electrophoresis gel step is further comprised of the step of scanning said light source to achieve uniform illumination of said electrophoresis gel.

* * * * *